United States Patent

Szäntay et al.

[11] 4,057,550
[45] Nov. 8, 1977

[54] NITROGEN-CONTAINING POLYCYCLIC COMPOUNDS

[75] Inventors: Csaba Szántay; Lajós Szabo; György Kalaus; Egon Kárpáti; Lászlo Szporny, all of Budapest, Hungary

[73] Assignee: Richter Gedeon Vegyeszeti Gyar Rt., Budapest, Hungary

[21] Appl. No.: 614,239

[22] Filed: Sept. 17, 1975

[30] Foreign Application Priority Data

Sept. 27, 1974  Hungary .................................. RI 547

[51] Int. Cl.² .................. C07D 471/02; C07D 455/02
[52] U.S. Cl. .......................... 260/293.55; 260/293.53; 260/294.9; 424/267
[58] Field of Search ...................... 260/293.53, 293.55

[56] References Cited

U.S. PATENT DOCUMENTS 3,454,583  7/1969  Kuehne ............................ 260/294.3
3,925,392  12/1975  Najer et al. .................... 260/293.53

OTHER PUBLICATIONS

Blaha et al., Coll. Czech. Chem. Comm. 33, 3833–3847 (1968).
Bartlett et al., J. Org. Chem. 28, 2197–2199 (1963).

*Primary Examiner*—John M. Ford
*Attorney, Agent, or Firm*—Toren, McGeady and Stanger

[57] ABSTRACT

New compounds of the general formula (I)

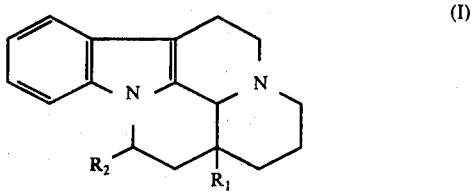

wherein $R_1$ stands for alkyl and $R_2$ stands for carboxy, a functional carboxy derivative or a group convertible into carboxy group or a functional derivative thereof, have been prepared by reducing a compound of the general formula

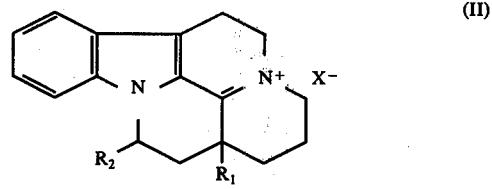

wherein $R_1$ and $R_2$ each have the same meanings as defined above and $X^-$ represents an anion derived from an acid, and optionally subjecting the obtained compound to hydrolysis. If desired, the racemic compounds of the general formula (I) can be resolved to yield the corresponding optically active isomers. The free bases of the general formula (I) can be converted into their pharmaceutically acceptable salts, or the salts can be treated with an alkaline agent to yield the free bases.

The compounds of the general formula (I) can be used in the therapy primarily as vasodilatating agents.

2 Claims, No Drawings

NITROGEN-CONTAINING POLYCYCLIC COMPOUNDS

This invention relates to new indolopyrido-naphthyridine derivatives and pharmaceutical compositions containing the same, as well as to a process for the preparation thereof.

The new compounds according to the invention can also be regarded as the derivatives of the alkaloid eburnamenine (J. Org. Chem. 28, 2197 /1963/). For this reason the new compounds according to the invention are termed in the following as the derivatives of eburnamenine.

Accordingly, the invention relates to new eburnamenine derivatives having the general formula (I) or salts or optically active isomers of the same

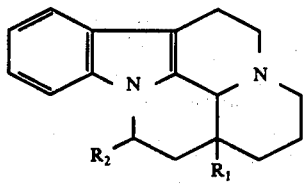

(I)

wherein
$R_1$ stands for alkyl group, and
$R_2$ stands for carboxy group, a functional carboxy derivative (preferably an ester group) or a group convertable into carboxy group or a functional derivative thereof (preferably cyano group).

Some of the eburnamenine-type compounds, such as vincamine and its derivatives, are known to possess valuable therapeutic effects.

In the compounds of the general formula (I) $R_1$ represents a straight-chained or branched alkyl group, preferably a lower alkyl group with 1 to 6 carbon atoms. Of these groups, e.g., the methyl, ethyl, n-propyl, isopropyl, n-butyl, isobutyl, tert-butyl, amyl, isoamyl and hexyl groups are to be mentioned. Particularly preferred are those compounds of the general formula (I), in which $R_1$ stands for ethyl.

$R_2$, when it stands for an ester group, may represent, e.g., an alkoxycarbonyl or aralkoxycarbonyl group. The alkoxycarbonyl groups contain preferably a straight-chained or branched $C_{1-6}$ alkoxy group; of these, e.g., the methoxycarbonyl, ethoxycarbonyl, n-propoxycarbonyl, n-butoxycarbonyl, isobutoxycarbonyl, tert-butoxycarbonyl, amyloxycarbonyl, isoamyloxycarbonyl, n-hexyloxycarbonyl and isohexyloxycarbonyl groups are to be mentioned. The preferred aralkoxycarbonyl groups are mono- or polycyclic, and contain a $C_{7-20}$ aralkoxy group; of these, e.g., the benzyloxycarbonyl, phenethoxycarbonyl, phenylpropoxycarbonyl, phenylbutoxycarbonyl, naphthylmethoxycarbonyl, naphthylethoxycarbonyl and naphthylburoxycarbonyl groups are to be mentioned.

The most preferred compounds of the general formula (I) are the ones in which $R_1$ stands for a lower alkyl group and $R_2$ represents carboxy, lower alkoxycarbonyl or cyano group.

Particularly preferred are those compounds of the general formula (I), in which $R_1$ stands for ethyl or n-butyl, and $R_2$ stands for methoxycarbonyl, ethoxycarbonyl or cyano.

The new compounds of the general formula (I), or their salts or optically active isomers, respectively, are prepared according to the invention as follows:

A compound of the general formula (II),

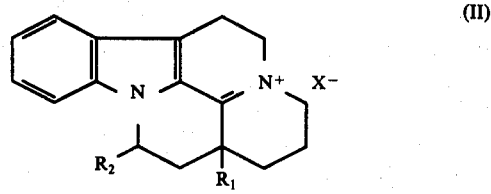

(II)

wherein $R_1$ and $R_2$ each have the same meanings as defined above and $X^-$ is an anion derived from an acid, is reduced, and, if desired, a thus-obtained compound of the general formula (I), wherein $R_1$ and $R_2$ each have the same meanings as defined above, is reacted with an acid, and/or, if desired, a compound of the general formula (I), wherein $R_1$ has the same meanings as defined above and $R_2$ is cyano or an ester group, is subjected to hydrolysis, and/or, if desired, a racemic compound of the general formula (I), wherein $R_1$ and $R_2$ each have the same meanings as defined above, is resolved to obtain the respective optically active substances.

The compounds of the general formula (II), used as starting substances in the above process, can be prepared by reacting a compound of the general formula (III),

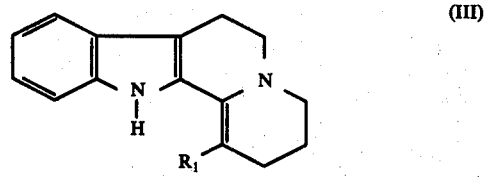

(III)

wherein $R_1$ has the same meanings as defined above, with a compound of the general formula (IV),

(IV)

wherein $R_2$ has the same meanings as defined above and Y is halogen, and, if desired, reacting a thus-obtained compound of the general formula (II), wherein $R_1$ and $R_2$ each have the same meanings as defined above and $X^-$ is a halide ion, with an acid, and/or, if desired, subjecting a compound of the general formula (II), wherein $R_1$ and $X^-$ each have the same meanings as defined above and $R_2$ is a cyano or an ester group, to hydrolysis.

The compounds of the general formula (II) are new substances, and are the subject of a separate patent application.

In the compounds of the general formula (II) $X^-$ may stand for an anion derived from any organic or inorganic acid. Of these anions, e.g., the following are to be mentioned: halides, such as fluoride, chloride, bromide and iodide, sulfate, phosphate, a perhalogenate, such as perchlorate and perbromate, acetate, propionate, oxalate, citrate, benzoate, naphthoate, maleate, succinate, salicylate, p-toluenesulfonate, etc. The preferred representatives of $R_1$ and $R_2$ in the compounds of the general formulae (II), (III) and (IV) are those listed in connection with the compounds having the general formula (I). In the compounds of the general formula (IV) Y may stand for any halogen atom, such as fluorine, bromine, chlorine or iodine, but Y represents preferably a chlorine or bromine atom.

Any reducing agent capable of saturating an endocyclic double bond without hydrogenating simultaneously the $R_2$ = cyano group can be used in accordance with the process of the invention. The reduction is performed preferably with a chemical reducing agent or by catalytic hydrogenation.

In chemical reduction, preferably a complex metal hydride, particularly a borohydride, such as lithium or sodium borohydride, is used as reducing agent.

Of the complex metal hydrides the borohydrides are particularly preferred, because of their outstanding selectivity. When a borohydride is used as reducing agent, the reaction is performed in a solvent or suspending agent which is inert towards the reaction. One may use to advantage an aliphatic alcohol, such as methanol, or an aqueous alcohol, such as aqueous methanol.

The borohydride is added to the reaction mixture in excess, preferably in an amount of 1.5 to 7 moles per one mole of the starting substance. The reaction time and temperature are not critical, and their optimum values depend primarily on the reactivity of the starting substance used. The reaction is performed generally at about 0° C, by stirring the reaction mixture for about 30 minutes to about 3 hours.

According to a preferred method of the invention a compound of the general formula (II), wherein $R_1$, $R_2$ and $X^-$ each have the same meanings as defined above, is suspended in an inert solvent, preferably in an aliphatic alcohol, the suspension is cooled to about 0° C, and the borohydride (preferably sodium borohydride) is added to the suspension in small portions at the same temperature.

The reaction mixture can be processed by methods known per se, e.g., by acidifying and concentrating the reaction mixture, dissolving the residue in water, rendering the solution alkaline, extracting the alkaline mixture, and evaporating the extract to dryness.

If catalytically activated hydrogen is used as reducing agent, preferably a metal belonging to the subgroups of the Periodic System, such as palladium, platinum, nickel, iron, copper, cobalt, chromium, zinc, molybdenum, tungsten, etc. or an oxide or sulfide thereof is used as hydrogenating catalyst.

The catalysts to be used in the process of the invention can be prepared, e.g., by reducing their stable oxides with hydrogen directly in the reaction vessel. This method can be used, e.g., when finely divided palladium or platinum is to be applied as hydrogenating catalyst. Alternately, catalysts prepared by acidic or alkaline leaching of one metal from a binary alloy, such as Raney-nickel, can be used as well. The catalytic hydrogenation can also be performed in the presence of a supported catalyst; this enables to decrease considerably the amount of the expensive noble metals necessary for the reduction. Of the supports, e.g., carbon (particularly charcoal), silicium dioxide, aluminum oxide, and the sulfates and carbonates of alkaline earth metals are to be mentioned.

When the reduction is performed with catalytically activated hydrogen, one employs preferably palladium (particularly palladium-on-charcoal) or Raney-nickel as catalyst. The catalysts are always selected in accordance with the reaction conditions and the characteristics of the substance to be hydrogenated.

The catalytic reduction is performed in a solvent inert towards the reaction, such as an alcohol, ethyl acetate, glacial acetic acid, etc., or a mixture of such solvents. The aliphatic alcohols, such as methanol and ethanol, proved to be the most preferred solvents. If platinum oxide is used as catalyst, the reaction is performed preferably in a neutral or slightly acidic medium, whereas if Raney-nickel is applied, the reaction is conducted preferably in a neutral or alkaline medium.

The temperature, pressure and time of the catalytic reduction may vary within wide limits depending on the starting substances. It is preferable, however, to conduct the reaction at room temperature and under atmospheric pressure until the cessation of the hydrogen uptake. The hydrogen uptake ceases generally within 10 minutes to 5 hours.

The reaction mixture is processed in a manner known per se, e.g., by filtering the mixture and evaporating the filtrate to dryness.

The catalytic hydrogenation is performed preferably as follows: a catalyst (preferably palladium-on-charcoal) is washed with a mixture of water and the solvent used in the hydrogenation process (preferably methanol), and the washed catalyst is prehydrogenated. Thereafter a solution of the appropriate starting substance of the general formula (II), or a salt thereof, in the above solvent is added to the pre-treated catalyst, and the resulting mixture is hydrogenated, preferably at room temperature and under atmospheric pressure, until the hydrogen uptake ceases.

The product is generally separated from the reaction mixture as a crystalline solid. If, however, an amorphous powder or an oily substance is obtained, it can usually be crystallized very easily from a suitable solvent, such as an aliphatic alcohol, e.g., methanol, ethanol, etc.

The free bases of the general formula (I) can be converted into their acid addition salts. For this purpose preferably pharmaceutically acceptable mineral or organic acids, such as hydrogen halides (e.g., hydrochloric acid, hydrobromic acid, etc.), phosphoric acid, organic carboxylic acids (e.g., acetic acid, propionic acid, glycolic acid, maleic acid, succinic acid, tartaric acid, citric acid, salicylic acid, benzoic acid, etc.), alkylsulfonic acids (e.g., methanesulfonic acid), arylsulfonic acids (e.g., p-toluenesulfonic acid) etc., can be used. In turn, the acid addition salts can be treated with a base to yield the compounds of the general formula (I) in the form of the free bases.

The salt formation is performed preferably in an inert solvent, particularly in an aliphatic alcohol, such as methanol. The base of the general formula (I) is dissolved in the solvent, and the mixture is acidified slightly (to about pH = 6) with the appropriate acid. The acid is added preferably in small portions. Thereafter the separated salt of the starting base is isolated from the reaction mixture.

The compounds of the general formula (I), in which $R_1$ has the same meanings as defined above and $R_2$ stands for cyano or an ester group, as well as their salts, can be subjected optionally to hydrolysis, to obtain the respective compounds of the general formula (I), in which $R_2$ stands for carboxy, or the salts thereof.

The hydrolysis is performed preferably in an inert organic solvent, particularly in an aliphatic alcohol, such as ethanol, with a base, preferably an inorganic base, such as an alkali metal hydroxide (e.g., sodium hydroxide) as hydrolyzing agent.

The reaction mixtures can be processed by methods known per se. The actual method of processing depends on the nature of the starting substances, the end-products, the solvents, etc. If the product separates at the end of the reaction, it is isolated by filtration, whereas if it remains dissolved, the solution is evaporated to dryness, preferably under reduced pressure.

The compounds of the general formula (I) contain an asymmetric carbon atom, they may exist therefore in the form of optically active isomers. The synthesis according to the invention yields racemic end-products, which can be resolved into the individual optically active isomers by known methods.

If desired, the compounds according to the general formula (I) can be subjected to additional purification steps, such as recrystallization. As solvents for recrystallization, e.g., aliphatic alcohols, such as methanol or ethanol, ketones, such as acetone, aliphatic esters, particularly alkyl alkanecarboxylates, such as ethyl acetate, acetonitrile, etc., furthermore the mixtures of these solvents, e.g., a mixture of ethyl acetate and ether, etc., can be used.

The process of the invention enables to produce the compounds of the general formula (I) with high yields and in forms easy to identify. The analytical data of the obtained compounds are in good agreement with the calculated values. The structures of the obtained products can be confirmed further by IR and NMR spectroscopy.

The compounds of the general formula (I) and their pharmaceutically acceptable acid addition salts possess valuable biological properties. According to the results of the tests carried out on narcotized dogs, the compounds possess significant vasodilatating effects. The compounds increase primarily the cerebral blood flow, but some of them effectively increase the blood flow of the limbs as well. In comparison with the significant increase of the blood flow, the temporary drop in blood pressure (lasting for about 1 to 2 minutes) and the increase of heart rate are relatively small.

The tests were performed on dogs narcotized with chloralose-urethane. The blood flow of the limbs was measured at the arteria femoralis, whereas the cerebral blood flow was investigated by measuring the flow of the arteria carotis interna. The circulation resistance was calculated from the blood pressure and blood flow values.

The compounds under examination were administered in intravenous dosages of 1 mg./kg. The observed changes were expressed as percentages in relation to the controls. 6 animals were used in each of the tests, and the data of Table 1 are the mean values calculated for these groups.

For comparison purposes the respective data of apovincaminic acid ethyl ester, the most active of the compounds with related structures (see Hungarian Pat. No. 163,434) are also given.

Notes to Table 1:
1. blood flow of the limbs
2. circulation resistance of the limb blood vessels
3. cerebral blood flow
4. circulation resistance of the cerebral blood vessels
5. blood pressure
6. heart rate
A. 14,15-dihydro-14-methoxycarbonyl-eburnamenine
B. 14,15-dihydro-14-ethoxycarbonyl-eburnamenine
C. 14,15-dihydro-14-cyano-eburnamenine
D. 14,15-dihydro-14-cyano-21-ethyl-eburnamenine
Ref. apovincaminic acid ethyl ester Table 1

| Substance | (1) | (2) | (3) | (4) | (5) | (6) |
|---|---|---|---|---|---|---|
| Ref. | +58 | −35 | +16 | −20 | −28 | +14 |
| (A) | +107 | −31 | +28 | −31.2 | −17.8 | +20.4 |
| (B) | +80 | −45.7 | +27.9 | −22.7 | −14.3 | +12 |
| (C) | +70 | −52.2 | +32 | −45.5 | −44.6 | +2.7 |
| (D) | +98 | −50.2 | +94.3 | −41.4 | −6 | +19.3 |

As appears from the data of the Table, the new compounds according to the invention are about 1.5 times as active as the reference substance with respect to the increase of the blood flow in the limbs, whereas their activities exceed 1.5 to 6 times that of the reference substance with respect to the increase of the cerebral blood flow.

The effective intravenous or oral dosage of the new compounds may vary within about 0.1 to 2 mg./kg. body weight. It should be noted, however, that the actual dosage is always determined in accordance with the needs of the patient, thus in some instances dosages lower or higher than those mentioned above are to be applied.

The compounds of the general formula (I) or the pharmaceutically acceptable acid addition salts thereof can be converted into pharmaceutical compositions suitable for enteral or parenteral administration. These compositions may contain the new compounds according to the invention either alone or in combinations with other biologically active substances. When preparing the pharmaceutical compositions the active agents(s) is(are) admixed with conventional inert, non-toxic, pharmaceutically acceptable carriers and/or diluents. As carrier, e.g., water, gelatine, lactose, starch, magnesium stearate, talc, vegetable oils, gum arabic, polyalkylene glycols, vaseline, etc., can be used. The compositions may optionally contain conventional pharmaceutical auxiliary agents, such as preservatives, salts for adjusting the osmotic pressure, buffers, flavouring agents, etc. The pharmaceutical compositions can be prepared in conventional forms, e.g., as solid formulations (tablets, coated tablets, capsules, etc.) or as liquid preparations (e.g., solutions, suspensions, emulsions, etc.) The obtained compositions can be sterilized or subjected to other finishing operations, if necessary.

The invention is elucidated in detail by the aid of the following non-limiting Examples.

EXAMPLE 1

14,15-Dihydro-14-methoxycarbonyl-eburnamenine-(3β,16α)

a. A methanol suspension of 1 g. of palladium-on-carbon is prehydrogenated, and a solution of 1.0 g. (2.3 mmoles) of 3,4-dehydro-14,15-dihydro-14-methoxycarbonyleburnamenine perchlorate in 100 ml. of methanol is added to the suspension. The reaction mixture is hydrogenated at room temperature and under atmospheric pressure. After the uptake of the theoretical amount of hydrogen, which requires about one hour, i.e., when the hydrogen uptake ceases, the catalyst is filtered off, and the filtrate is evaporated in vacuo. The solidified residue is dissolved in distilled water, and the solution is rendered alkaline with saturated aqueous sodium carbonate solution. This operation is carried out under cooling. The obtained cloudy mixture of pH = 10 is extracted with 30 ml., 20 ml. and 10 ml. of dichloroethane. The organic solutions are combined, dried over magnesium sulfate, filtered, and the filtrate is evaporated in vacuo. The oily residue is crystallized from methanol. 0.55 g. (70.8%) of 14,15-dihydro-14-methoxycarbonylebur- namenine-(3β,16α) are obtained as a white, crystalline powder; m.p.: 117°–118° C.

Analysis: calculated for $C_{21}H_{26}N_2O_2$ (M = 338.43): C: 74.52% H: 7.74% N: 8.28%; found: C: 74.29% H: 7.77% N: 7.93%.

IR-spectrum (in KBr pellet): 2702–2770 cm$^{-1}$ (Bohlman bands), 1745 cm$^{-1}$ (=C=O).

NMR-spectrum (in deuterochloroform): 2.22–2.80 (4H, aromatic protons), 5.18 (1H, $CH_3O—CO—CH—N=$), 6.21

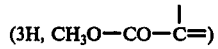

(3H, $CH_3O—CO—\overset{|}{C}=$)

and 9.26 (3H, —$CH_3$) ppm.

b. 6.25 g. (14.3 mmoles) of 3,4-dehydro-14,15-dihydro-14-methoxycarbonyl-eburnamenine perchlorate are suspended in 300 ml. of methanol, the suspension is cooled to 0° C, and 1.05 g. (27.8 mmoles) of sodium borohydride are added to the cooled suspension in small portions. After the addition the mixture is stirred for one hour, thereafter it is acidified to pH = 3 with 5 n hydrochloric acid. The reaction mixture is evaporated in vacuo, and the solid residue is dissolved in 200 ml. of distilled water. 80 ml. of dichloroethane are added to the solution, and the mixture is rendered alkaline (pH = 10) with 40% aqueous sodium hydroxide solution under cooling. The mixture is shaken, the organic phase is separated, and the aqueous phase is extracted with 30 ml. and 20 ml. of dichloroethane, respectively. The organic solutions are combined, dried over magnesium sulfate, filtered, and the filtrate is evaporated in vacuo. The oily residue is crystallized from methanol to obtain 3.05 g. (63.2%) of white, crystalline 14,15-dihydro-14-methoxycarbonyl-eburnamenine-(3β,16α); m.p.: 116°–118° C. The obtained compound is identical with the substance prepared according to paragraph (a).

EXAMPLE 2

14,15-Dihydro-14-ethoxycarbonyl-eburnamenine- (3β,16α)

4.90 g. (11.9 mmoles) of 3,4-dehydro-14,15-dihydro-14-ethoxycarbonyl-eburnamenine perchlorate are suspended in 250 ml. of methanol, the suspension is cooled to 0° C, and 2.0 g. (53 mmoles) of sodium borohydride are added to the stirred suspension in small portions. After the addition the mixture is stirred for one hour at 0° C, and then it is acidified to pH = 3 with 5 n hydrochloric acid. The mixture is concentrated in vacuo to a final volume of 20 ml., and 250 ml. of distilled water and 80 ml. of dichloroethane are added to the concentrate. The mixture is rendered alkaline (pH = 11) with 40% aqueous sodium hydroxide solution under cooling, thereafter it is shaken, and the phases are separated from each other. The organic phase is dried over magnesium sulfate, filtered, and the filtrate is evaporated in vacuo. The oily residue is crystallized from ethanol to obtain 2.15 g. (51.7%) of 14,15-dihydro-14-ethoxycarbonyl-eburnamenine-(3β,16α) as a white, crystalline powder melting at 104°–105° C.

Analysis: calculated for $C_{22}H_{28}N_2O_2$ (M = 352.45): C: 74.96% H: 8.01% N: 7.95%; found: C: 74.90% H: 8.08% N: 8.36%.

IR-spectrum (in KBr pellet): 2702–2857 cm$^{-1}$ (Bohlmann bands), 1750 cm$^{-1}$ (=C=O).

NMR-spectrum (in deuterochloroform): 2.43–3.02 (4H, aromatic protons), 5.38 (1H, $CH_3—CH_2—O—CO—CH—N=$), 5.71 (2H, —$CH_2—O—CO—$) and 9.23 (3H, alkyl -$CH_3$) ppm.

EXAMPLE 3

14,15-Dihydro-14-cyano-eburnamenine-(3β,16α)

2.0 g. (4.96 mmoles) of 3,4-dehydro-14,15-dihydro-14-cyano-eburnamenine perchlorate are suspended in 100 ml. of methanol, the suspension is cooled to 0° C, and 1.0 g. (26.5 mmoles) of sodium borohydride are added to the stirred suspension in small portions. After the addition the mixture is stirred for 1 hour, and then it is acidified to pH = 3 with 5 n hydrochloric acid. The reaction mixture is concentrated in vacuo to a final volume of 20 ml., and 100 ml. of distilled water and 60 ml. of dichloroethane are added to the concentrate. The pH of the mixture is adjusted to 11 with 40% aqueous sodium hydroxide solution under cooling, thereafter it is shaken, and the phases are separated from each other. The organic phase is dried over magnesium sulfate, filtered, and the filtrate is evaporated to dryness in vacuo. The solid residue is crystallized from methanol to obtain 1.20 g. (79.2%) of 14,15-dihydro-14-cyano-eburnamenine-(3β,16α) as a beige, crystalline powder; m.p.: 155°–156° C.

Analysis: calculated for $C_{20}H_{23}N_3$ (M = 305.41): C: 78.65% H: 7.59% N: 13.76%; found: C: 78.58% H: 7.70% N: 13.61%.

IR-spectrum (in KBr pellet): 2702–2760 cm$^{-1}$ (Bohlmann bands), 2280 cm$^{-1}$ (—CN).

NMR-spectrum (in DMSO-$d_6$): 2.48–3.02 (4H, aromatic protons), 4.72

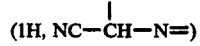

(1H, NC—$\overset{|}{CH}$—N=)

and 9.33 (3H, —$CH_3$) ppm.

EXAMPLE 4

14,15-Dihydro-14-methoxycarbonyl-21-ethyleburnamenine-(3β,16α)

5.0 g. (10.76 mmoles) of 3,4-dehydro-14,15-dihydro-14-methoxycarbonyl-21-ethyl-eburnamenine perchlorate are suspended in 200 ml. of methanol, the suspension is cooled to 0° C, and 2.50 g. (66.1 mmoles) of sodium borohydride are added in small portions. After the addition the mixture is stirred for one hour, and then it is acidified to pH = 3 with 5 n hydrochloric acid. The acidic mixture is concentrated in vacuo to a final volume of 30 ml., and 150 ml. of distilled water and 80 ml. of dichloroethane are added to the concentrate. The pH of the mixture is adjusted to 10 to 11 with 40% aqueous sodium hydroxide solution under cooling, thereafter it is shaken, and the phases are separated from each other. The organic phase is dried over magnesium sulfate, filtered, and the filtrate is evaporated in vacuo. The oily residue is crystallized from methanol to obtain 2.10 g. (53.2%) of 14,15-dihydro-14-methoxycarbonyl-21-ethyl-eburnamenine-(3β,16α) as a white, crystalline substance melting at 103°–104° C.

Analysis: calculated for $C_{23}H_{30}N_2O_2$ (M = 366.49): C: 75.37% H: 8.25% N: 7.64%; found: C: 75.36% H: 8.25% N: 7.71%.

IR-spectrum (in KBr pellet): 2752–2880 cm$^{-1}$ (Bohlmann bands), 1747 cm$^{-1}$ (=C=O)

NMR-spectrum (in deuterochloroform): 2.28–2.94 (4H, aromatic protons), 5.28 (1H, CH$_3$O—CO—CH—N=) and 6.13 (3H, —OCH$_3$) ppm.

EXAMPLE 5

14,15-Dihydro-14-cyano-21-ethyl-eburnamenine-(3β,16α)

3.50 g. (8.10 mmoles) of 3,4-dehydro-14,15-dihydro-14-cyano-21-ethyl-eburnamenine perchlorate are suspended in 200 ml. of methanol, the suspension is cooled to 0° C, and 1.75 g. (46.2 mmoles) of sodium borohydride are added in small portions. After the addition the mixture is stirred at the same temperature for one hour, and then it is acidified to pH = 3 with 5 n hydrochloric acid. The mixture is concentrated in vacuo to a final volume of 30 ml., and 150 ml. of distilled water and 70 ml. of dichloroethane are added to the concentrate. The mixture is rendered alkaline (pH = 10) with 40% aqueous sodium hydroxide solution under cooling, thereafter it is shaken, and the phases are separated from each other. The organic phase is dried over magnesium sulfate, filtered, and the filtrate is evaporated in vacuo. The residue is crystallized from 10 ml. of methanol to obtain 2.20 g. (81.2%) of 14,15-dihydro-14-cyano-21-ethyl-eburnamenine-(3β,16α) as a crystalline substance melting at 139°–141° C.

Analysis: calculated for C$_{22}$H$_{23}$N$_3$ (M = 333.45): C: 79.24% H: 8.16% N: 12.60%; found: C: 79.23% H: 7.93% N: 12.51%.

IR-spectrum (in KBr pellet): 2680–2790 cm$^{-1}$ (Bohlmann-bands), 2295 cm$^{-1}$ (—CN).

NMR-spectrum (in deuterochloroform): 2.18–2.91 (4H, aromatic protons) and 5.02

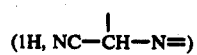

(1H, NC—CH—N=)

ppm.

EXAMPLE 6

14,15-Dihydro-14-carboxy-eburnamenine a. A mixture of 0.75 g. (2.13 mmoles) of 14,15-dihydro-14-methoxycarbonyl-eburnamenine, 0.2 g. (5 mmoles) of sodium hydroxide and 15 ml. of 95% ethanol is refluxed for 4 hours. The reaction mixture is evaporated in vacuo, the residue is dissolved in 8 ml. of distilled water, and the pH of the solution is adjusted to 7 with 20% aqueous acetic acid. The separated substance is filtered off. 0.65 g. (94.3%) of 14,15-dihydro-14-carboxy-eburnamenine are obtained; m.p.: 234°–236° C. IR-spectrum (in KBr pellet): 1580–1670 cm$^{-1}$ (broad band system).

b. 0.2 g. (5 mmoles) of sodium hydroxide are added to the solution of 1 g. (3.28 mmoles) of 14,15-dihydro-14-cyano-eburnamenine in 15 ml. of 95% ethanol, and the mixture is refluxed for 8 hours. Thereafter the mixture is processed as described in paragraph (a) to obtain the same substance with the same properties.

EXAMPLE 7

3,4-Dehydro-14,15-dihydro-14-methoxycarbonyl-eburnamenine perchlorate (starting substance)

4.0 g. (11.4 mmoles) of 1-ethyl-1,2,3,4,6,7-hexahydro-12H-indolo(2,3-a) quinolizinium perchlorate (J. Am. Chem. Soc. 87, 1580/1968/) are suspended in 40 ml. of dichloromethane, and 30 ml. of distilled water and 8 ml. of 2 n aqueous sodium hydroxide solution are added to the stirred suspension under argon atmosphere. The reaction mixture is stirred for 10 minutes, thereafter the organic phase is separated and dried over anhydrous potassium carbonate. The drying agent is filtered off, 4 ml. of freshly distilled methyl α-bromo-acrylate are added to the filtrate, the mixture is flushed with argon, and it is allowed to stand at room temperature. An exothermic reaction sets in and the colour of the solution turns lighter. After 2 days of standing at room temperature the solution is evaporated in vacuo, and the oily residue is repeatedly triturated with petroleum ether. The obtained solid is dissolved in 10 ml. of methanol, and 2.0 ml. of 70% perchloric acid solution are added. The crystallization is initiated by scraping the wall of the flask, thereafter the mixture is maintained in refrigerator. The separated crystals are filtered off and washed with cold methanol to obtain 4.65 g. of a yellow substance.

This substance is recrystallized from a 8-fold volume of methanol to obtain 4.20 g. (84.6%) of 3,4-dehydro-14,15-dihydro-14-methoxycarbonyl eburnamenine perchlorate as a yellow, crystalline substance melting at 188°–190° C.

Analysis: calculated for C$_{21}$H$_{25}$N$_2$O$_6$Cl (M = 436.88): C: 57.73% H: 5.76% N: 6.41%; found: C: 57.93% H: 5.66% N: 6.50%.

IR-spectrum (in KBr pellet): 1748 cm$^{-1}$ (=C=O) and 1642 cm$^{-1}$ (=C=N+=).

EXAMPLE 8

3,4-Dehydro-14,15-dihydro-14-cyano-eburnamenine-perchlorate starting substance)

2.0 g. (5.67 mmoles) of 1-ethyl-1,2,3,4,6,7-hexahydro-12H-indolo(2,3-a) quinolizinium perchlorate are suspended in 20 ml. of dichloromethane, and 15 ml. of distilled water and 4 ml. of a 2 n aqueous sodium hydroxide solution are added to the stirred suspension under argon atmosphere. The reaction mixture is stirred for 10 minutes, thereafter the organic phase is separated and dried over anhydrous potassium carbonate. The drying agent is filtered off, 2.0 ml. (25.2 mmoles) of α-chloro-acrylonitrile are added to the filtrate, the mixture is flushed with argon, and it is allowed to stand at room temperature. An exothermic reaction sets in and the color of the solution turns lighter. After 2–3 days of standing at room temperature the reaction mixture is evaporated in vacuo, the solid residue is dissolved in 6 ml. of hot methanol, and a 70% perchloric acid solution is added. A light yellow, crystalline substance starts immediately to separate. The mixture is kept in refrigerator, the crystals are filtered off, and the obtained 2.25 g. of crude substance is recrystallized from a three-fold volume of methanol. 2.0 g. (87.8%) of 3,4-dehydro-14,15-dihydro-14-cyano-eburnamenine perchlorate are obtained as a light yellow, crystalline substance melting at 240° to 241° C under decomposition.

Analysis: calculated for C$_{20}$H$_{22}$N$_3$ClO$_4$ (M = 403.85): C: 59.47% H: 5.49% N: 10.44% found: C: 59.54% H: 5.51% N: 10.23%.

IR-spectrum (in KBr pellet): 2320 cm$^{-1}$ (—CN), 1641 cm$^{-1}$ (=C=N+=).

EXAMPLE 9

3,4-Dehydro-14,15-dihydro-14-methoxycarbonyl-21-ethyl-eburnamenine perchlorate (starting substance)

5.0 g. (13.3 mmoles) of 1-n-butyl-1,2,3,4,6,7-hexahydro-12H-indolo(2,3-a)quinolizinium perchlorate are suspended in 50 ml. of dichloromethane, and 40 ml. of distilled water and 10 ml. of a 2 n aqueous sodium hydroxide solution are added to the stirred suspension under argon atmosphere. The reaction mixture is stirred for 10 minutes, thereafter the organic phase is separated and dried over anhydrous potassium carbonate. The drying agent is filtered off, 5.0 ml. of freshly distilled methyl α-bromo-acrylate are added to the filtrate, the mixture is flushed with argon, and it is allowed to stand at room temperature. After 3 days of standing at room temperature the reaction mixture is evaporated in vacuo, the obtained red, oily residue is dissolved in 10 ml. of hot methanol, the solution is filtered, and 2.30 ml. of a 70% perchloric acid solution is added dropwise to the filtrate. Upon cooling, a yellow, crystalline substance separates from the solution. This substance is filtered off, washed with a small amount of methanol, and the crude product, weighing 4.75 g., is recrystallized from a 15-fold volume of methanol. 4.20 g. (68.0%) of 3,4-dehydro-14,15-dihydro-14-methoxycarbonyl-21-ethyl-eburnamenine perchlorate are obtained as a dense, crystalline substance melting at 147°–148° C.

Analysis: calculated for $C_{23}H_{29}N_2ClO_6$ (M = 464.93): C: 59.41% H: 6.28% N: 6.02%; found: C: 59.30% H: 6.20% N: 6.20%.

IR-spectrum (in KBr pellet): 1752 cm$^{-1}$ (=C=O), 1648 cm$^{-1}$ (=C=N+=).

EXAMPLE 10

3,4-Dehydro-14,15-dihydro-14-cyano-21-ethyl-eburnamenine perchlorate (starting substance)

5.0 g. (13.3 mmoles) of 1-n-butyl-1,2,3,4,6,7-hexahydro-12H-indolo(2,3-a)quinolizinium perchlorate are suspended in 50 ml. of dichloromethane, and 40 ml. of distilled water and 10 ml. of a 2 n aqueous sodium hydroxide solution are added to the stirred suspension under argon atmosphere. The reaction mixture is stirred for some minutes, thereafter the organic phase is separated and dried over anhydrous potassium carbonate. The drying agent is filtered off, 5.0 ml. of α-chloroacrylonitrile are added to the filtrate, the mixture is flushed with argon, and it is allowed to stand at room temperature. An exothermic reaction sets in, and the colour of the solution turns lighter. After 3 days of standing at room temperature the reaction mixture is evaporated in vacuo, the residue is dissolved in 15 ml. of hot methanol, and 2.20 ml. of a 70% perchloric acid solution is added. Upon cooling, a yellow, crystalline substance separates from the solution. The mixture is kept in a refrigerator, and subsequently the crystals are filtered off. 3.50 g. (61.0%) of 3,4-dehydro-14,15-dihydro-14-cyano-21-ethyl-eburnamenine perchlorate are obtained; m.p.: 259°–260° C under decomposition.

Analysis: calculated for $C_{22}H_{26}N_3ClO_4$ (M = 431.9): C: 61.17% H: 6.15% N: 9.69%; found: C: 61.34% H: 6.15% N: 9.69%.

IR-spectrum (in KBr pellet): 2360 cm$^{-1}$ (—CN), 1648 cm$^{-1}$ (=C=N+=).

What we claim is:
1. 14,15-Dihydro-14-cyano-eburnamenine-(3β,16α).
2. 14,15-Dihydro-14-cyano-21-ethyl-eburnamenine-(3β,16α).

* * * * *